US010524657B2

(12) United States Patent
Jeglorz (10) Patent No.: US 10,524,657 B2
(45) Date of Patent: Jan. 7, 2020

(54) SYSTEM AND CONTROLLING METHOD THEREOF FOR PERFORMING MEASUREMENTS OF AN EYE (71) Applicant: Wavelight GmbH, Erlangen (DE)

(72) Inventor: Tobias Jeglorz, Stein (DE)

(73) Assignee: WaveLight GmbH, Erlanden (DE)

( * ) Notice: Subject to any disclaimer, the term of this patent is extended or adjusted under 35 U.S.C. 154(b) by 510 days.

(21) Appl. No.: 15/003,341

(22) Filed: Jan. 21, 2016

(65) Prior Publication Data
US 2016/0213251 A1 Jul. 28, 2016

(30) Foreign Application Priority Data
Jan. 28, 2015 (DE) .................. 10 2015 001 078

(51) Int. Cl.
A61B 3/14 (2006.01)
A61B 3/00 (2006.01)
A61B 3/10 (2006.01)
A61B 3/18 (2006.01)

(52) U.S. Cl.
CPC .............. A61B 3/14 (2013.01); A61B 3/0025 (2013.01); A61B 3/0083 (2013.01); A61B 3/102 (2013.01); A61B 3/18 (2013.01)

(58) Field of Classification Search
CPC ........... A61B 3/14; A61B 3/0025; A61B 3/12; A61B 3/102; A61B 3/0058; A61B 3/1225; A61B 3/113; A61B 3/1025; A61B 3/0008; A61B 3/0091; A61B 3/145; A61B 3/0041; A61B 3/1015; A61B 3/117; A61B 3/1005; A61B 3/103; A61B 3/112

USPC ....... 351/206, 246, 221, 205, 208, 209, 200, 351/202, 216, 219
See application file for complete search history.

(56) References Cited

U.S. PATENT DOCUMENTS

| 2007/0171367 | A1* | 7/2007 | Sebastian ............... A61B 3/00 351/206 |
| 2007/0291277 | A1* | 12/2007 | Everett ............... A61B 3/102 356/497 |
| 2013/0188130 | A1* | 7/2013 | Inoue ............... A61B 3/0083 351/206 |
| 2013/0265547 | A1 | 10/2013 | Higuchi |

FOREIGN PATENT DOCUMENTS

| DE | 102010050695 A1 | 5/2012 |
| DE | 102013200926 A1 | 7/2013 |
| JP | H05-285113 A | 11/1993 |

(Continued)

Primary Examiner — Thomas K Pham
Assistant Examiner — Sharrief Broome (57) ABSTRACT A system for performing measurements of an eye comprises: a measurement tool that measures the eye, at least one rest that maintains a facial measurement position and defines a centering rest portion that maintains a lateral facial measurement position; an adjuster mechanism that moves an objective of the measurement tool relative to the eye; and a processing unit configured to control the system. The unit controls the system to position, for a first eye, the objective at a predefined first pre-scan position; scan the objective away from the first pre-scan position until the system detects a pupil of the first eye; and trigger one or more measurements of the first eye dependent on the system detecting the pupil of the first eye.

15 Claims, 7 Drawing Sheets (56) References Cited

FOREIGN PATENT DOCUMENTS

| JP | 2014-147493 A | 8/2014 |
|----|---------------|--------|
| WO | 2014091992 A1 | 6/2014 |
| WO | 2014103646 A1 | 7/2014 |

* cited by examiner

SYSTEM AND CONTROLLING METHOD THEREOF FOR PERFORMING MEASUREMENTS OF AN EYE

CROSS REFERENCE TO RELATED APPLICATIONS

This application claims priority to German Patent Application Serial Number 10 2015 001 078.6, filed 28 Jan. 2015, titled "SYSTEM AND CONTROLLING METHOD THEREOF FOR PERFORMING MEASUREMENTS OF AN EYE," which is hereby incorporated by reference in its entirety.

TECHNICAL FIELD

The present disclosure generally relates to a controlling method of a system for performing measurements of an eye and said system using the method.

BACKGROUND

For eye surgery (e.g., LASIK surgery), measurement information such as corneal tissue shape and thickness and eye position may be obtained by a measurement tool such as a diagnostic device (e.g., an aberrometer, autorefractor, a keratometer, a corneal topographer, or an Optical Coherence Tomographer) or therapeutic device performing the eye surgery.

Typically, said devices must be adjusted to the specific dimensions of the patient. For example, when performing diagnostic measurements on a patient for refractive surgery, a user may operate a joystick of a diagnostic device to find a patient's eye. Said joystick may control a stage or other means that positions the diagnostic device, relative to the patient, for obtaining diagnostic measurements.

To explain further, a camera may be used to find a patients eye, an image of which is displayed to the diagnostic device user. The diagnostic device may further display symbols to provide assistance regarding the direction that the system needs to be moved, via the joystick, for obtaining optimum positioning for measurement. Once the position is obtain, measurement processes are triggered for obtaining various optical properties of the patients eye.

It may be necessary to adjust the stage when patients slightly move before, during, and/or after the measurement process or even leave from and return to the measurement position. In such cases, the stage needs to be reconfigured for subsequent measurements.

SUMMARY

Accordingly, there is a need for systems and methods that can quickly and consistently place measurement tools in appropriate measurement positions.

According to one aspect, a system for performing measurements of an eye comprises: a measurement tool for performing measurements of the eye, the measurement tool including an objective and implementing an image capturing function using the objective; at least one rest designed to maintain a facial measurement position, the at least one rest defining a centering rest portion designed to maintain a lateral facial measurement position; an adjuster mechanism adapted to move the objective relative to the eye; and a processing unit configured to control the system to: position, via the adjuster mechanism and for a first eye, the objective at a predefined first pre-scan position; scan, via the adjuster mechanism, the objective away from the first pre-scan position until the system detects a pupil of the first eye; and trigger one or more measurements of the first eye via the measurement tool dependent on the system detecting the pupil of the first eye.

In certain embodiments, the processing unit is further configured to control the system to: position, via the adjuster system and for a second eye, the objective at a predefined second pre-scan position that is different from the first pre-scan position; scan, via the adjuster system, the objective away from the second pre-scan position until the system detects a pupil of the second eye; trigger one or more measurements of the second eye via the measurement tool dependent on the system detecting the pupil of the second eye.

In certain embodiments, the second pre-scan position mirrors the first scan position with respect to a vertical axis passing through the centering rest portion.

In certain embodiments, the processing unit is configured to control the system to scan, via the adjuster mechanism, the objective away from the first pre-scan position along a vertical direction.

In certain embodiments, the processing unit is configured to control the system to scan, via the adjuster mechanism, the objective away from the second pre-scan position along a vertical direction.

In certain embodiments, the measurement tool includes an image sensor for capturing images.

In certain embodiments, the at least one rest comprises a chin rest, wherein an image captured by the measurement tool in the first pre-scan position of the objective covers a facial area higher than a statistical maximum pupil height or lower than a statistical minimum pupil height relative to the chin rest.

In certain embodiments, an image captured by the measurement tool in the second pre-scan position of the objective covers a facial area higher than a statistical maximum pupil height or lower than a statistical minimum pupil height relative to the chin rest.

In certain embodiments, an image captured by the measurement tool in the first pre-scan position of the objective covers a facial area having a lateral position and lateral width appropriate to accommodate statistical variations of a pupillary distance from a vertical center axis passing through the centering rest portion.

In certain embodiments, the processing unit is configured to control the system to record coordinate information of at least one of: a scan position related to the system detecting the pupil of the first eye, and a scan position related to the system triggering the one or more measurements of the first eye.

In certain embodiments, the processing unit is configured to control the system to record coordinate information of at least one of: a scan position related to the system detecting the pupil of the second eye, and a scan position related to the system triggering the one or more measurements of the second eye.

In certain embodiments, the processing unit is configured to control the system to retrieve the recorded coordinate information and re-adjust the objective based on the retrieved coordinate information.

In certain embodiments, the at least one rest comprises a chin rest adapted to be positionally adjustable via the adjuster mechanism, wherein the processing unit is configured to control the system to record position information of the chin rest in association with the coordinate information retrieve the recorded position information and re-adjust, via the adjuster mechanism, the chin rest in accordance with the retrieved position information.

In certain embodiments, the processing unit is configured to control the system to finely adjust the objective in at least the Z direction for focusing on a detected pupil of an eye.

In certain embodiments, the processing unit is configured to control the system to retract the objective away from the first eye after completion of the triggered one or more measurements of the first eye.

In certain embodiments, the measurement tool comprises an optical coherence tomography device configured to emit a beam of measurement radiation through the objective.

According to another aspect, a non-transitory computer-readable memory contains a program which, when loaded in a computer or processor or running on a computer or processor, causes the computer processor to control the above system, said control comprising: positioning, via the adjuster mechanism and for a first eye, the objective at a predefined first pre-scan position; scanning, via the adjuster mechanism, the objective away from the first pre-scan position until the system detects a pupil of the first eye; and triggering one or more measurements of the first eye via the measurement tool dependent on the system detecting the pupil of the first eye.

According to yet another aspect, a controlling method of a system for performing measurements of an eye is provided, wherein the system includes a measurement tool for performing measurements of the eye, the measurement tool including an objective and implementing an image capturing function using the objective, at least one rest designed to maintain a facial measurement position, the at least one rest defining a centering rest portion designed to maintain a lateral facial measurement position, and an adjuster mechanism adapted to move the objective relative to the eye, the method comprising: positioning, via the adjuster mechanism and for a first eye, the objective at a predefined first pre-scan position; scanning, via the adjuster mechanism, the objective away from the first pre-scan position until the system detects a pupil of the first eye; and triggering one or more measurements of the first eye via the measurement tool dependent on the system detecting the pupil of the first eye.

BRIEF DESCRIPTION OF THE DRAWINGS

Embodiments of the present disclosure will be further detailed based on the following figures, of which.

DETAILED DESCRIPTION

In the following, for purposes of explanation and not limitation, specific details are set forth, such as particular sequences of steps, components and configurations, in order to provide a thorough understanding of the present invention. It will be apparent to one skilled in the art that the present invention may be practiced in other embodiments that depart from these specific details.

Figure 1:
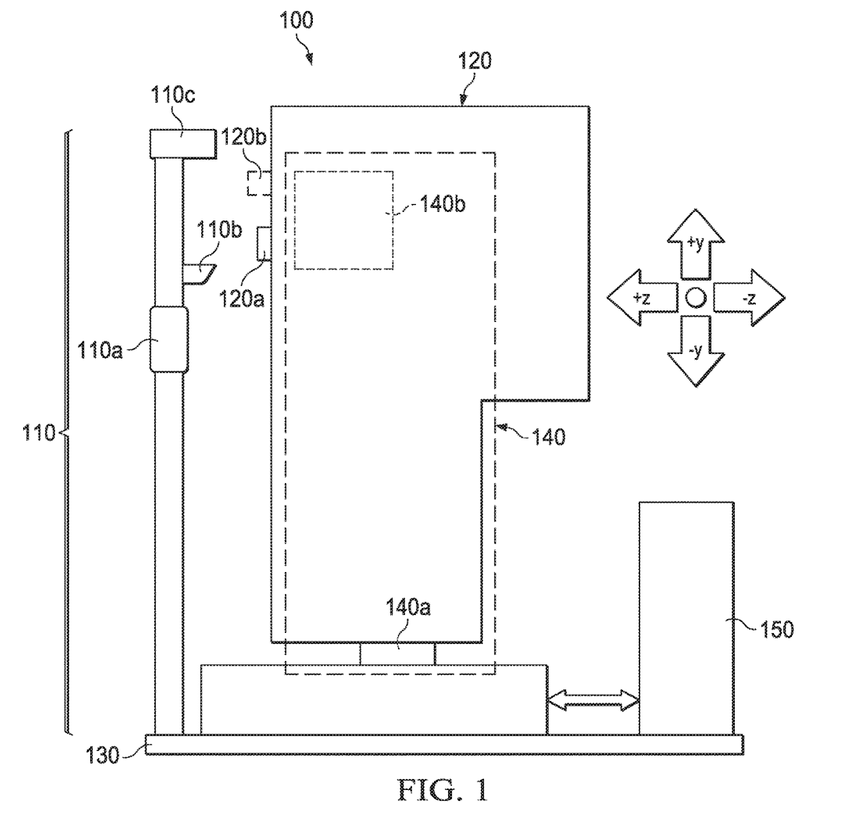
FIG. 1 schematically illustrates an example diagnostic system.

In FIG. 1, system 100 is schematically shown. System 100 includes patient interface 110. Patient interface 110 includes height adjuster 110a, chin rest 110b and forehead rest 110c, Adjuster 110a adjusts the height of at least chin rest 110b via, for example, mechanical or electromechanical means. For example, adjuster 110a may be mechanical fastener that is locked and unlocked by a patient or user turning adjuster 110a so to adjust and fix the height of chin rest 110b.

Although two rests are shown, some embodiments may include a single rest that maintains a measurement position of the patient. For example, chin rest 110b may be enlarged to engage a larger portion of a patient's face so to prevent facial pitch movement, e.g., head nodding.

Chin rest 110b and forehead rest 110c are arranged and structured for coupling with a patient's face such that the patient faces towards optics 120a of measurement tool 120 for measuring an eye. Measurement tool 120 may be an Optical Coherence Tomographer. Chin rest 110b and forehead rest 110c may be further arranged and structured for defining and maintaining a lateral facial measurement position with respect to the measurement tool 120, as explained in more detail below.

Table 130 supports both patient interface 110 and measurement tool 120. Adjuster mechanism 140 may include adjusters 140a and 140b operable to move measurement tool 120 and/or optics 120a (e.g., a scanning camera objective) and 120b, in the X, Y, and Z directions relative to patient interface 110. For example, optics 120a may be operable to move in the X, Y, and Z directions relative to patient interface 110 independently of adjuster 140a via adjuster 140b. More particularly, optics 120a may be coupled to electromechanical means of adjuster 140b operable for making said adjustments.

In another example embodiment, adjuster 140b may be operable to move optics 120a in the Z directions independently of adjuster 140a, whereas adjuster 140a may be operable in at least the X and Y directions, thereby providing X, Y, and Z directional movement capabilities for optics 120a, Example adjusters include, but are not limited to, translation stages, translation slides, actuators, and optical focus units for focusing an optical component.

Optics 120a may include an objective that is both a scanning camera objective used for pupa detection (described in more detail below) and a focusing objective for performing measurements an eye. The focusing objective may direct a measurement beam, such as a laser beam for OCT imaging, onto the eye and receive reflected radiation or be used in other diagnostic procedures, Examples of a scanning camera objective include an infrared camera for detecting Purkinje reflexes and a camera for taking images in the visible wavelength range.

In alternative embodiments, optics 120a may include the scanning camera objective and optics 120b may include the focusing objective. In this case, optics 120a and 120b may move in unison in the X, Y, and Z directions relative to patient interface 110 via adjuster 140a and/or adjuster 140b, as described above.

System 100 may further includes computer system 150 that is communicatively coupled with adjuster mechanism 140 via wired and/or wireless means. Computer system 150 may include non-transitory computer readable memory for storing instructions for controlling, via a processor, other components of the diagnostic system (e.g., adjuster mechanism 140) according to present embodiments.

Figure 2:
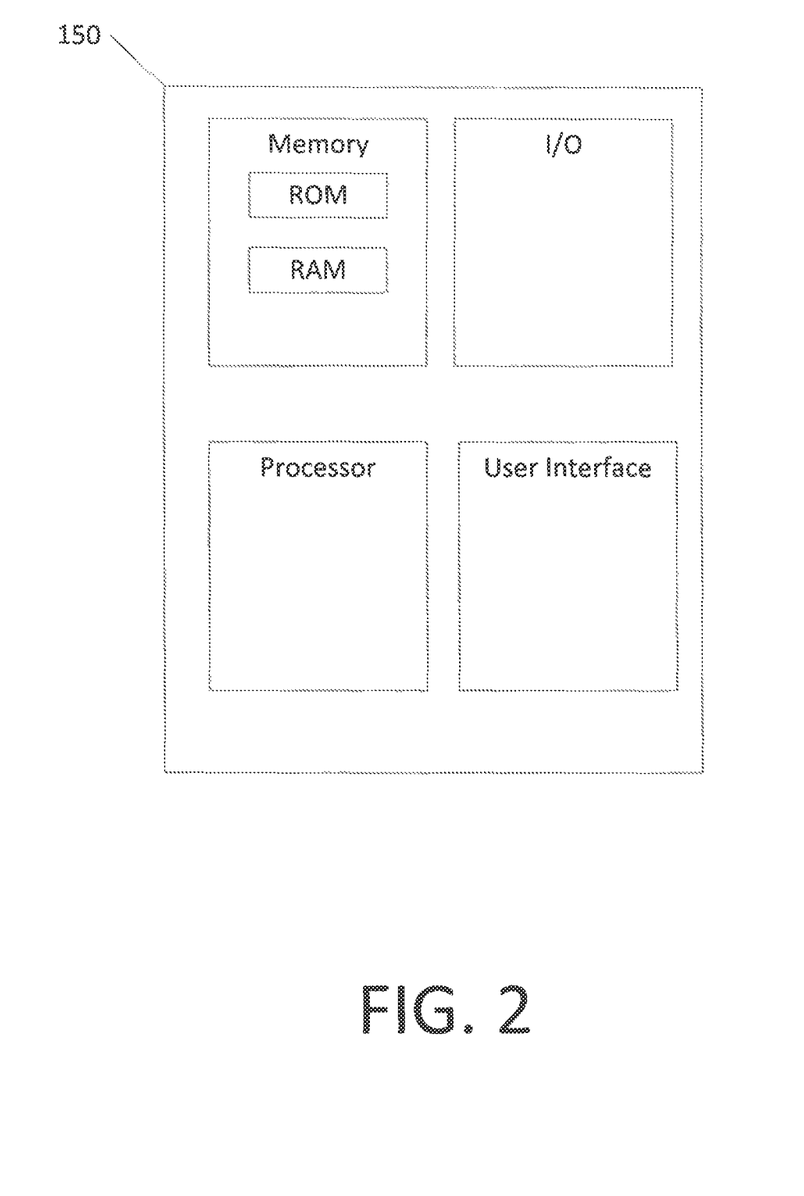
FIG. 2 schematically illustrates an example computer system.

As shown in FIG. 2, computer system 150 may include memory modules such as ROM and RAM, one or more processors, I/O modules for communicating within and outside computer system 150, and user interface modules, such as a joystick, display, and keyboard. Embodiments include housing computer system 150 within measurement tool 120.

Figure 3A:
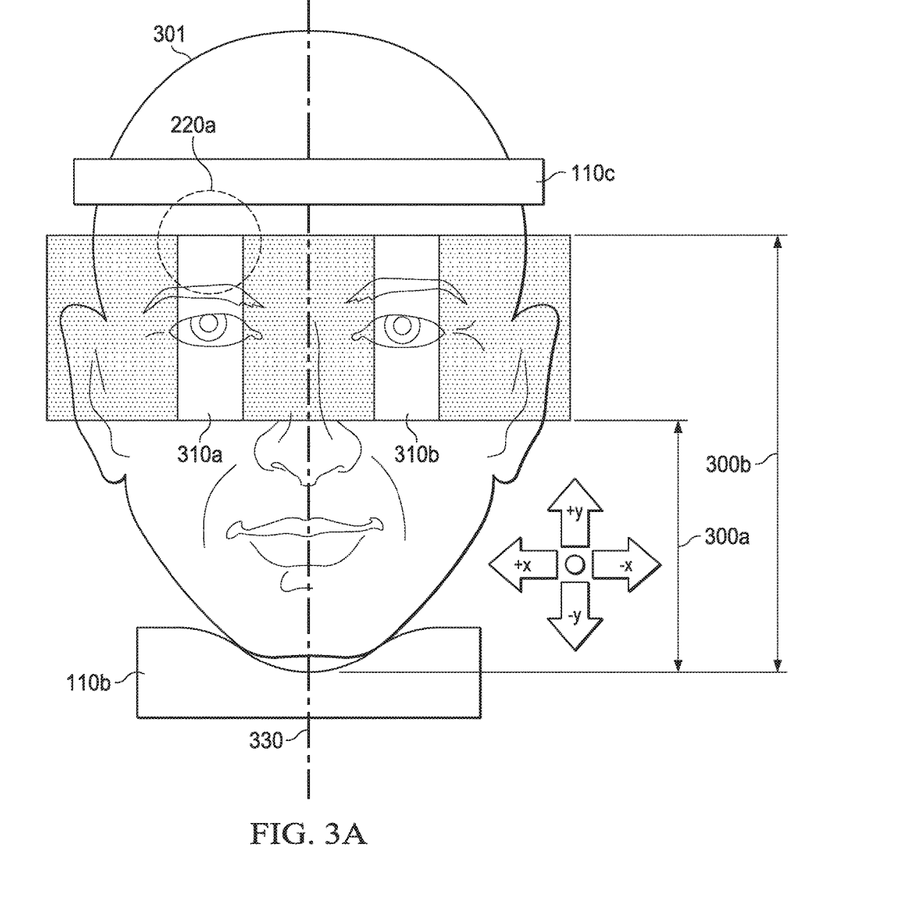
FIGS. 3A and 3B schematically illustrate an example diagnostic system and a patient.
Figure 3B:
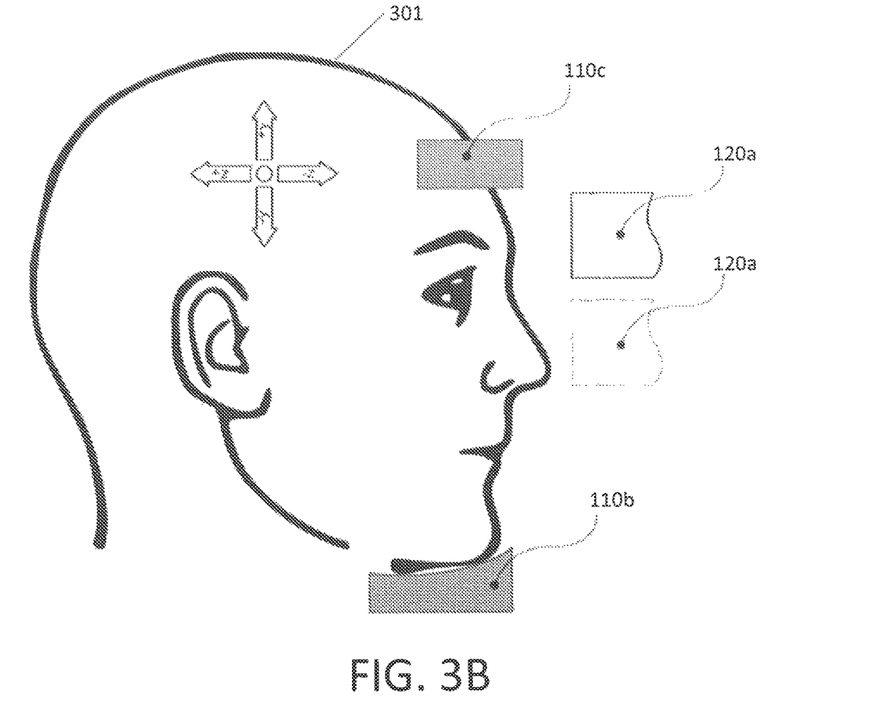

FIGS. 3A and 3B show patient 301 engaged with rests 110b and 110c, Rest 110b includes a centering rest portion indicating a facial centered measurement position, wherein a portion of the centering rest portion includes a depression coinciding with notational axis 330 showing the presumed axis about which a patient's face is substantially symmetrical (e.g., facial features symmetric with respect to the presumed axis), Although not explicitly shown, rest 110c may include a similar depression.

Maximum and minimum scan positions 300a and 300b define a vertical scan range for optics 120a to scan, Scan positions 300a and 300b may define the lower and upper limits of the scan range in the Y direction. The chosen limits allow system 100 to accommodate for variations of pupillary height within the human population with respect to, for example, rest 110b (i.e., the distance between rest 110b and a patient's pupil with the patient is engaged with rests 110b and 110c), For example, scan position 300b may be higher than the maximum height of a pupil, as measured from rest 110b. As shown in FIG. 3A, scan positions 300a and 300b are relative to rest 110b, but embodiments also include defining search ranges relative to rest 110c.

Scan positions 300b and 300a may be a pre-scan position of optics 120a that captures an image that covers a facial area higher than a statistical maximum pupil height, as shown by field of view (FOV) 220a, or lower than a statistical minimum pupil height relative to the chin rest, Maximum and minimum pupil heights may be derived from a number of sources. Example sources include DIN 33402 ("Ergonomics—human body dimensions—Section 2: values for geometrical tolerances for head and eye position"), which provides values applicable to patients between the age of 18 to 65. Similar data can be found in the ANSUR database, a 1988 anthropometric survey of military personnel, and the NHANES National Health and Nutrition Examination Survey database.

Similarly, a horizontal search range may be defined by a minimum and maximum pupillary distance, as shown by pupillary bands 310a and 310b. Rests 110b and 110c may be arranged and structured for defining and maintaining a lateral facial measurement position with respect to measurement tool 120. For example, the lateral facial measurement position may maintain a position such that the viewing field of optics 120a accommodates for variations in pupillary distance within the human population. In other words, a pre-scan position of optics 120a may capture an image that covers a facial area having a lateral position and lateral width appropriate to accommodate statistical variations of a pupillary distance from a vertical center axis passing through the centering rest portion.

To explain further, the distance between pupils within the human population typically varies somewhere between 60 mm and 70 mm. Thus, a maximum variation may be about 10 mm as for the total distance from the left eye to the right eye and about 5 mm as for the distance of a pupil of one eye with respect to a center axis passing through the center of rest 110b and/or rest 110c. Thus, pupil bands 310a and 310b may each be 5 mm wide and FOV 220a of optics 120a is wider than pupil bands 310a and 310b.

Thus, embodiments include arranging a patient and optics 120a such that FOV 220a is as wide as or wider than pupillary bands 310a and 310b during pupil detection. Embodiments may also account for iris dimension in determining the full range in which an eye must be located.

Taking these parameters into account, optics 120a may operate from a predefined pre-scan position, as shown in FIGS. 3A and 3B, corresponding to scan position 300b and scan towards scan position 300a until an eye is detected. Further, the pre-scan position may position optics 120a such that FOV 220a is as wide as or wider than pupillary bands 310a and 310b during pupil detection. For example, within a 5 mm wide pupil band, optics 120a may operate from a predefined pre-scan position with FOV 220a being wider than 5 mm and the pre-scan position corresponds to a mid-point between the extremes of pupil band 310a or pupil band 310b.

Figure 4A:
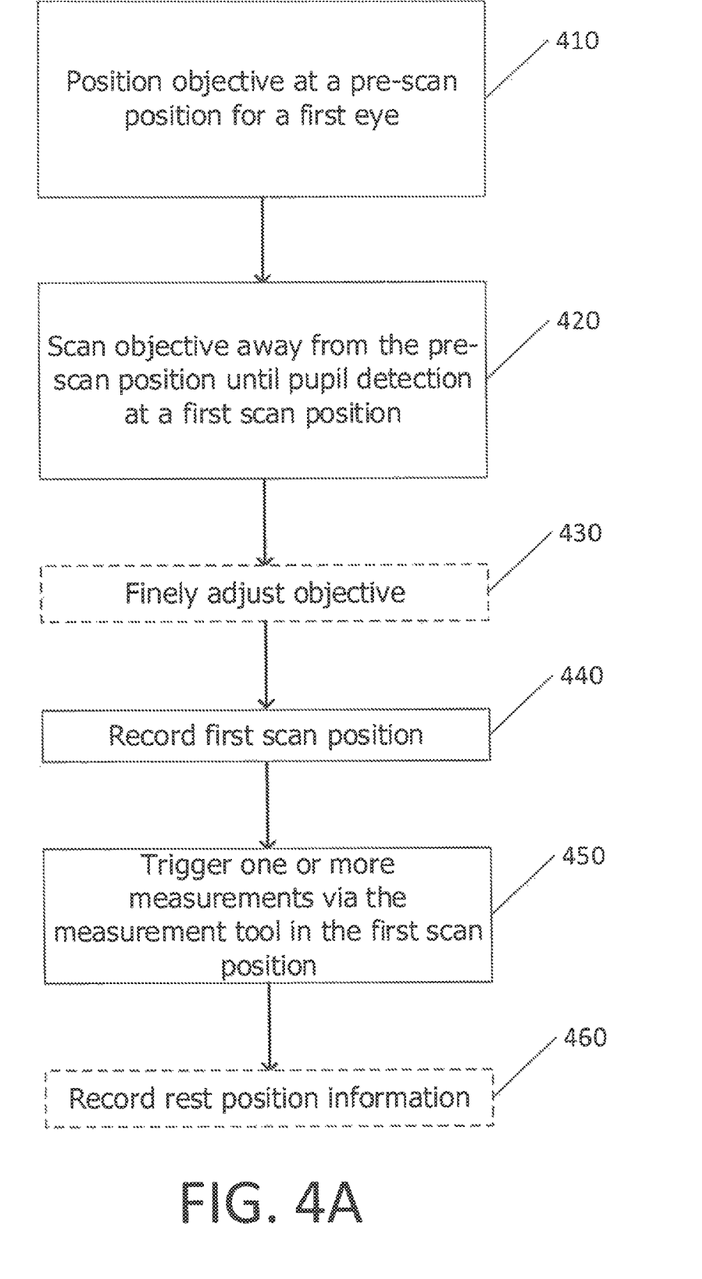
FIGS. 4A to 4C are flow charts illustrating method embodiments for controlling a system for performing measurements of an eye by a measurement tool.
Figure 4B:
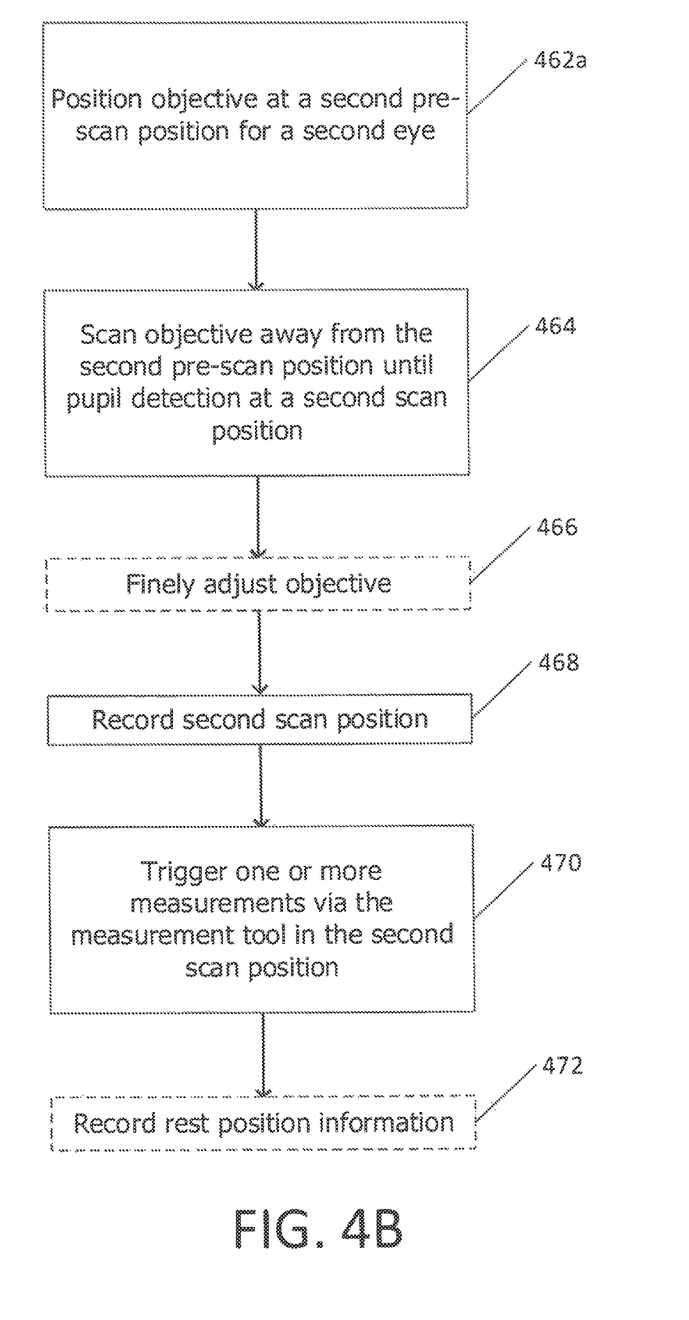
Figure 4C:
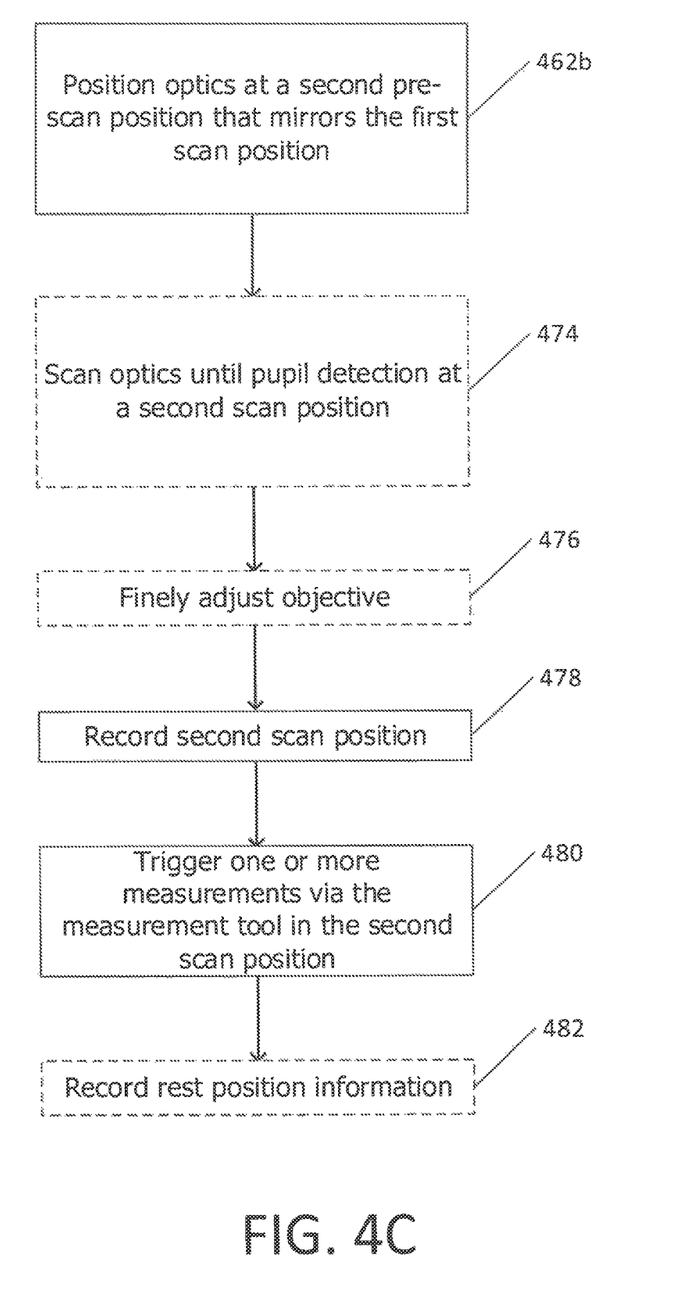

FIGS. 4A to 4C are flow charts illustrating method embodiments for controlling a system for performing measurements of an eye by a measurement tool, the measurement tool including an objective and implementing an image capturing function using the objective.

In FIG. 4A, step 410 positions, via the adjuster mechanism and for a first eye, an objective at a predefined first pre-scan position. An image captured via an objective (e.g., an objective of optics 120a) in the first pre-scan position may cover a facial area of a patient that is higher than a statistical maximum pupil height or lower than a statistical minimum pupil height relative to a rest (e.g., rests 110b or 110c). The captured image may also cover a facial area having a lateral position and lateral width appropriate to accommodate statistical variations of a pupillary distance from a vertical center axis passing through the centering rest portion, as explained in detail with FIGS. 3A and 3B.

Step 420 scans, via the adjuster mechanism, the objective away from the pre-scan position and towards the opposite extreme until the system detects a pupil of the first eye at a first scan position. That is, if the objective at the first pre-scan position 1a captures an image that covers a facial area that is higher than a statistical maximum pupil height relative to a rest, the objective is scanned towards, at least with respect to the Y direction, a facial area that is lower than a statistical minimum pupil height.

FIG. 3B shows optics 120a at the first pre-scan position, which captures an image that covers a facial area that is higher than a statistical maximum pupil height relative to a rest, and scanning optics 120a in the negative V direction until an eye or pupil is detected. Embodiments also include other scan patterns such as a raster scan pattern. Pupil detection may include template matching among other techniques known to one skilled in the art.

Step 430 finely adjusts the objective for the detected eye via the adjuster mechanism or other means, and typical involves an objective adjustment in the Z direction for focusing on the detected eye, but may also include fine adjustment in the X and V directions too for accurate eye measurements. Step 440 records the first scan position. Said position may be expressed as XV coordinates within an XV space in particular if the scans follow a constant Z coordinate (e.g., Z is known and constant for the scan of step 420). The position may also be expressed as XYZ coordinates within a three-dimensional space.

Thus, the recorded scan position may be the scan position of an objective of the optics upon pupil detection or the scan position after focusing. In other words, system embodiments include systems configured to record a coarse V position for quickly detecting a pupil in subsequent measurement sessions, but necessitate focusing and fine adjustments for measurements in the subsequent sessions. Alternatively or additionally, the system records the scan position after focusing or other fine adjustments.

Step 450 triggers one or more measurements of the first eye via the optical tool in the first scan position. Step 460 records a rest position. For example, the adjusted height of rest 110b may be recorded for later use such as reconfiguring a patient interface such that rest 110b is placed at the same position as in a previous measurement session. Said rest position may be recorded as a scalar value or a value within an XY or XYZ coordinate system.

In FIG. 4B, the method may continue by step 462a positioning, via an adjuster mechanism and for a second eye, the objective at a predefined second pre-scan position. That is, the objective is moved to the non-scanned half of a patient's face, and an image captured via the objective in the second pre-scan position may cover a facial area of a patient that is higher than a statistical maximum pupil height or lower than a statistical minimum pupil height relative to a rest. Embodiments may include retracting the objective or measurement tool in the Z direction (i.e., away from a patient's face) before switching sides so to avoid a collision between the objective or measurement tool and the patient (e.g., a patient's nose).

Step 464 scans, via the adjuster mechanism, the objective away from the second pre-scan position and towards the opposite extreme until the system detects a pupil of the second eye at a second scan position, similar to step 420. Further, step 466 corresponds to step 430 for the second eye. Step 468 records the second scan position in a manner as described for step 440. Step 470 triggers one or more measurements of the second eye via the measurement tool in the second scan position. Step 472 records the rest position information as explained in relation to step 460.

FIG. 4C provides an alternative set of steps to FIG. 4B. For example, step 462b positions, via the adjuster mechanism, the objective at a second pre-scan position that mirrors the first scan position with respect to an axis passing through the centering rest portion. This step is based on the assumption that the second eye is at or near the same pupillary height and at a symmetrical pupillary distance as the first eye (i.e., the first and second eyes exhibit reflection or mirror symmetry with respect to axis 330 of FIG. 3A).

Step 474 scans, via the adjuster mechanism, the objective until the system detects a pupil of a second eye at a second scan position. Step 474 typically includes small adjustments as the second pre-scan position should be at or near a position corresponding to the second eye.

Step 476 corresponds to step 430 for the second eye, Step 478 records the second scan position in a manner as described for step 440, Step 480 triggers one or more measurements measuring the optical properties of the second eye via the optical tool in the second scan position. Step 482 records the rest position information as explained in relation to step 460.

Although embodiments of the proposed technique have been illustrated in the accompanying drawings and described in the description, it will be understood that the invention is not limited to the embodiments disclosed herein. In particular, the proposed technique is capable of numerous rearrangements, modifications and substitutions without departing from the scope of the invention as set forth and defined by the following claims.

Furthermore, those skilled in the art will recognize that boundaries between the above described modules (e.g., computer 150) are merely illustrative. The multiple modules may be combined into a single module, a single module may be distributed in additional modules and modules may be executed at least partially overlapping in time. Moreover, alternative embodiments may include multiple instances of a particular module, and the order of modules may be altered in various other embodiments.

However, other modifications, variations and alternatives are also possible. The specifications and drawings are, accordingly, to be regarded in an illustrative rather than in a restrictive sense.

The invention may also be implemented in a computer program for running on a computer circuit, at least including code portions for performing steps of a method according to the invention when run on a programmable apparatus, such as a computer circuit or enabling a programmable apparatus to perform functions of a device or circuit according to the invention.

A computer program is a list of instructions such as a particular application program and/or an operating circuit. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer circuit.

The computer program may be stored internally on computer readable storage medium or transmitted to the computer circuit via a computer readable transmission medium. All or some of the computer program may be provided on transitory or non-transitory computer readable media permanently, removably or remotely coupled to an information processing circuit. The computer readable media may include, for example and without limitation, any number of the following: magnetic storage media including disk and tape storage media; optical storage media such as compact disk media (e.g., CD-ROM, CDR, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.; and data transmission media including computer networks, point-to-point telecommunication equipment, and carrier wave transmission media, just to name a few.

A computer process typically includes an executing (running) program or portion of a program, current program values and state information, and the resources used by the operating circuit to manage the execution of the process, An operating circuit (OS) is the software that manages the sharing of the resources of a computer and provides programmers with an interface used to access those resources, An operating circuit processes circuit data and user input, and responds by allocating and managing tasks and internal circuit resources as a service to users and programs of the circuit.

The computer circuit may for instance include at least one processing unit, associated memory and a number of input/output (I/O) devices. When executing the computer program, the computer circuit processes information according to the computer program and produces resultant output information via devices.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner.

Likewise, single connections carrying multiple signals may be separated out into various different connections carrying subsets of these signals. Therefore, many options exist for transferring signals.

The invention claimed is:

1. A system for performing measurements of an eye, comprising:
   a measurement tool configured to measure the eye, the measurement tool including an objective used to capture images;
   at least one chin rest designed to maintain a facial measurement position, the at least one rest defining a centering rest portion designed to maintain a lateral facial measurement position;
   an adjuster mechanism adapted to move the objective relative to the eye; and
   a processing unit configured to control the system to:
      position, via the adjuster mechanism and for a first eye, the objective at a predefined first pre-scan position;
      scan, via the adjuster mechanism, the objective away from the first pre-scan position until the system detects a pupil of the first eye; and
      trigger one or more measurements in an image captured of the first eye via the measurement tool dependent on the system detecting the pupil of the first eye;
      position, via the adjuster system and for a second eye, the objective at a predefined second pre-scan position that is different from the first pre-scan position;
      scan, via the adjuster system, the objective away from the second pre-scan position until the system detects a pupil of the second eye; and
      trigger one or more measurements in an image captured of the second eye via the measurement tool dependent on the system detecting the pupil of the second eye;
   wherein the image captured by the measurement tool in the first pre-scan position of the objective covers a facial area higher than a statistical maximum pupil height or lower than a statistical minimum pupil height relative to the chin rest; and
   wherein the image captured by the measurement tool in the second pre-scan position of the objective covers a facial area higher than a statistical maximum pupil height or lower than a statistical minimum pupil height relative to the chin rest.

2. The system of claim 1, wherein the second pre-scan position mirrors the first scan position with respect to a vertical axis passing through the centering rest portion.

3. The system of claim 1, wherein the processing unit is configured to control the system to scan, via the adjuster mechanism, the objective away from the first pre-scan position along a vertical direction.

4. The system of claim 1, wherein the processing unit is configured to control the system to scan, via the adjuster mechanism, the objective away from the second pre-scan position along a vertical direction.

5. The system of claim 1, wherein the measurement tool includes an image sensor for capturing images.

6. The system of claim 1, wherein an image captured by the measurement tool in the first pre-scan position of the objective covers a facial area having a lateral position and lateral width appropriate to accommodate statistical variations of a pupillary distance from a vertical center axis passing through the centering rest portion.

7. The system of claim 1, wherein the processing unit is configured to control the system to record coordinate information of at least one of: a scan position related to the system detecting the pupil of the first eye, and a scan position related to the system triggering the one or more measurements of the first eye.

8. The system of claim 1, wherein the processing unit is configured to control the system to record coordinate information of at least one of: a scan position related to the system detecting the pupil of the second eye, and a scan position related to the system triggering the one or more measurements of the second eye.

9. The system of claim 7, wherein the processing unit is configured to:
   control the system to retrieve the recorded coordinate information; and
   readjust the objective based on the retrieved coordinate information.

10. The system of claim 7, wherein:
    the at least one rest comprises a chin rest adapted to be positionally adjustable via the adjuster mechanism; and
    the processing unit is configured to:
       control the system to record position information of the chin rest in association with the coordinate information;
       retrieve the recorded position information; and
       readjust, via the adjuster mechanism, the chin rest in accordance with the retrieved position information.

11. The system of claim 1, wherein the processing unit is configured to control the system to finely adjust the objective in at least the Z direction for focusing on a detected pupil of an eye.

12. The system of claim 1, wherein the processing unit is configured to control the system to retract the objective away from the first eye after completion of the triggered one or more measurements of the first eye.

13. The system of claim 1, wherein the measurement tool comprises an optical coherence tomography device configured to emit a beam of measurement radiation through the objective.

14. A non-transitory computer-readable memory containing a program which, when loaded in a computer or processor or running on a computer or processor, causes the computer processor to control a system including a measurement tool configured to measure the eye, the measurement tool including an objective used to capture images, at least one chin rest designed to maintain a facial measurement position, the at least one rest defining a centering rest portion designed to maintain a lateral facial measurement position, and an adjuster mechanism adapted to move the objective relative to the eye, the control comprising:
   positioning, via the adjuster mechanism and for a first eye, the objective at a predefined first pre-scan position;
   scanning, via the adjuster mechanism, the objective away from the first pre-scan position until the system detects a pupil of the first eye; and
   triggering one or more measurements in an image captured of the first eye via the measurement tool dependent on the system detecting the pupil of the first eye;
   positioning, via the adjuster system and for a second eye, the objective at a predefined second pre-scan position that is different from the first pre-scan position;
   scanning, via the adjuster system, the objective away from the second pre-scan position until the system detects a pupil of the second eye; and triggering one or more measurements in an image captured of the second eye via the measurement tool dependent on the system detecting the pupil of the second eye;

wherein the image captured by the measurement tool in the first pre-scan position of the objective covers a facial area higher than a statistical maximum pupil height or lower than a statistical minimum pupil height relative to the chin rest; and wherein the image captured by the measurement tool in the second pre-scan position of the objective covers a facial area higher than a statistical maximum pupil height or lower than a statistical minimum pupil height relative to the chin rest.

15. A method of performing measurements of an eye in a system that includes a measurement tool configured to measure the eye, the measurement tool including an objective used to capture images, at least one chin rest designed to maintain a facial measurement position, the at least one rest defining a centering rest portion designed to maintain a lateral facial measurement position, and an adjuster mechanism adapted to move the objective relative to the eye, the method comprising:

positioning, via the adjuster mechanism and for a first eye, the objective at a predefined first pre-scan position;

scanning, via the adjuster mechanism, the objective away from the first pre-scan position until the system detects a pupil of the first eye; and triggering one or more measurements in an image captured of the first eye via the measurement tool dependent on the system detecting the pupil of the first eye;

positioning, via the adjuster system and for a second eye, the objective at a predefined second pre-scan position that is different from the first pre-scan position;

scanning, via the adjuster system, the objective away from the second pre-scan position until the system detects a pupil of the second eye; and triggering one or more measurements in an image captured of the second eye via the measurement tool dependent on the system detecting the pupil of the second eye;

wherein the image captured by the measurement tool in the first pre-scan position of the objective covers a facial area higher than a statistical maximum pupil height or lower than a statistical minimum pupil height relative to the chin rest; and wherein the image captured by the measurement tool in the second pre-scan position of the objective covers a facial area higher than a statistical maximum pupil height or lower than a statistical minimum pupil height relative to the chin rest.

* * * * *